(12) United States Patent
Roell et al.

(10) Patent No.: US 10,428,299 B2
(45) Date of Patent: Oct. 1, 2019

(54) MIXING DEVICE FOR MIXING THE CONTENTS OF A CONTAINER

(71) Applicant: Sartorius Stedim Biotech GmbH, Goettingen (DE)

(72) Inventors: Marcel Roell, Maur (CH); Daniel Hoepli, Balterwil (CH)

(73) Assignee: Sartorius Stedim Biotech GmbH (DE)

( * ) Notice: Subject to any disclaimer, the term of this patent is extended or adjusted under 35 U.S.C. 154(b) by 149 days.

(21) Appl. No.: 15/325,520

(22) PCT Filed: May 13, 2015

(86) PCT No.: PCT/EP2015/000992
§ 371 (c)(1),
(2) Date: Jan. 11, 2017

(87) PCT Pub. No.: WO2016/008556
PCT Pub. Date: Jan. 21, 2016

(65) Prior Publication Data
US 2017/0159001 A1      Jun. 8, 2017

(30) Foreign Application Priority Data
Jul. 14, 2014   (EP) .................................... 14002424

(51) Int. Cl.
*C12M 1/00*       (2006.01)
*C12M 3/06*       (2006.01)
*C12M 3/00*       (2006.01)

(52) U.S. Cl.
CPC ............ *C12M 27/16* (2013.01); *C12M 23/14* (2013.01); *C12M 23/46* (2013.01)

(58) Field of Classification Search
CPC .............................. C12M 27/16; C12M 23/14
See application file for complete search history.

(56) References Cited

U.S. PATENT DOCUMENTS 5,371,329 A  * 12/1994  Fillaud ................ A61M 1/0245
                                                           128/DIG. 13
6,190,913 B1 *  2/2001  Singh .................. B01F 11/0017
                                                           435/383

(Continued)

FOREIGN PATENT DOCUMENTS

DE      10 2005 007 512      9/2005
EP            1 173 542       4/2005

(Continued)

OTHER PUBLICATIONS

International Search Report dated Jun. 29, 2015.

*Primary Examiner* — Anshu Bhatia
(74) *Attorney, Agent, or Firm* — Gerald E. Hespos; Michael J. Porco; Matthew T. Hespos (57) ABSTRACT

A mixing device for mixing contents of a container has a support for supporting the container and a moving device connected to the support for moving the support and mixing the contents of the container. The support has a positioning device to position the container so that a removal side of the container is arranged substantially along a predetermined line of the support. The support is pivotable about a removal pivot axis to move the container into a removal position. The removal pivot axis is at an angle of over 0° to 45° to the predetermined line of the support so that the container can be moved from the mixing position by pivoting the support about the removal pivot axis into the removal position where the removal side is on a lower side of the container and inclined toward a removal region of the container.

11 Claims, 5 Drawing Sheets

(56) References Cited

U.S. PATENT DOCUMENTS

2013/0244322 A1 9/2013 Henon et al.
2013/0316446 A1* 11/2013 Andersson ............. C12M 23/14
435/305.1

FOREIGN PATENT DOCUMENTS

WO 00/66706 11/2000
WO 2012/115581 8/2012

* cited by examiner

MIXING DEVICE FOR MIXING THE CONTENTS OF A CONTAINER

BACKGROUND

1. Field of the Invention

The present invention relates to a mixing device for mixing the contents of a container.

2. Description of the Related Art

Containers for blending or circulating substances are used in many industrial fields. In the production of culture media for microorganisms or in controlled biotechnological processes such as cell cultivation the blending or the circulation of the container contents is particularly important. Because of the different initial concentrations of the substances as well as the metabolic activity of the microorganisms during the cultivation, local concentration changes of the most varied chemical components in the media batch or of nutrients, oxygen and the metabolites produced occur during the cultivation. In order to ensure the same or at least controlled concentration conditions in the entire container, it is necessary to blend or circulate the liquid or suspension in the container during the entire process.

The use of flexible disposable bioreactors made of foils is continually gaining in importance in particular with regard to the constantly increasing requirements for the sterility of the processes in bioprocess engineering in comparison to rigid containers made of glass or stainless steel. In addition to good sterilizability, foil bags offer further advantages such as cost-effective production, simple and space-saving storage, the best possible safety with regard to contamination and the omission of costly cleaning after use.

The blending of the contents of the flexible disposable bioreactor takes place both mechanically with the aid of agitator elements and also by means of the motion of the container with the liquid itself contained therein. In particular, when disposable flexible containers are used, it is considered advantageous to employ mixers without agitators, since no holes through the container wall are necessary for driving agitator elements. Depending upon the type of movement, such mixers are known as rockers, platform shakers, tumble mixers, circular shakers, vibratory shakers, horizontal shakers, orbital shakers, etc.

Depending upon the field of use, flexible containers can have different sizes, wherein larger containers can have volumes of several liters. Most pre-filled containers are usually arranged on plate-shaped or dish-shaped movable supports, and they are fixed on the supports, for example, by means of clamps or hooks or other releasable fastening means. The supports are driven and generate the mixing movement of the contents of the container. In this case the support carries out, for example, a rocking movement about a horizontal position.

In order to remove the contents from the bags again, the supports with the bags fixed thereon can be moved into an almost vertical position. Filling of the containers in the vertical position is also optionally possible.

WO 2012/115581 A1 discloses a bioreactor with a mixing device, in which a container support carries out a rocking movement about a horizontal rocking axis for mixing the contents of a container. A set-up axis, around which the container support can be pivoted in order to set up the container support, is arranged on a front end of the container support, wherein the set-up axis extends parallel to the rocking axis. In order to simplify the removal of products from the container, the container support in the set-up state can be inclined toward a corner of the container about a second tilting axis which extends perpendicular to the set-up axis. However, due to the provision of a set-up axis, on the one hand, and a tilting axis perpendicular thereto, on the other hand, the design of the mixing device is complex and disadvantageous.

The object of the present invention is to provide an improved mixing device which can move a container in a simple manner into an advantageous filling or removal position.

This object is achieved by the subject matter of the independent claim. Advantageous embodiments are disclosed by the dependent claims.

SUMMARY

According to the present invention, a mixing device is provided for mixing the contents of a container, and comprises: a container support for supporting the container; and a moving device, which for movement of the container support is connected to the container support in order to be able to mix the contents of the container in a mixing position; wherein the container support has a positioning device which is designed to position the container in a predetermined or predeterminable position on the container support, so that a removal side of the container is arranged substantially along a predetermined line of the container support, wherein the container support is mounted so as to be pivotable about a removal pivot axis relative to the moving device in order to be able to move the container which can be positioned thereon into a removal position, wherein the removal pivot axis is arranged at a pivot axis angle of over 0° to 45° to the predetermined line of the container support in such a way that the container which can be positioned thereon can be moved from the mixing position by means of a pivoting movement of the container support about the removal pivot axis into the removal position in which the removal side is located on the lower side of the container and also inclined toward a removal region of the container.

The container may in particular be a bioreactor container, which may be made from a foil material. Such a container can be designed as a bag with edges welded on at least two opposing sides. The container can have a predetermined bearing surface, on which the container can be placed in a stable manner on a horizontal surface. The contact surface can in particular be one of its largest surfaces or side faces. The contact surface and/or the surface opposite the contact surface can have openings and connections for feed conduits and/or discharge conduits and/or sensors. If the feed and/or discharge conduits are located on the contact surface, the container support also has corresponding openings for the connected conduits. The container can be arranged with its contact surface on the container support. In plan view the container can have a substantially rectangular shape with four side edges. In particular, the container can be symmetrical in plan view, which is advantageous for a uniform movement of the contents of the container during mixing. The container has at least a removal side. The removal side can be a substantially straight lateral edge of the container, wherein a lateral edge of the container interior is intended. The removal side designates the side of the container which is provided for collection and for removal of the contents of the container and in particular the products which have formed in the container. The removal region of the container can be arranged in one of the two corners of the removal side. An outlet from which the contents of the container can be discharged can be arranged at the removal region.

For removal, the container positioned on the container support is preferably moved together with the container support into the removal position. However, filling of the container via the feed conduits arranged on the container is likewise possible in this position.

The contents of the container may be a liquid or a suspension. The container can also contain a gas or gases. The contents of the container are mixed or circulated by means of the mixing device, so that in particular good oxygen blending can be ensured in cell cultivation.

The container support is configured in such a way that the container can be arranged thereon. The container support can be formed in such a way that the container, with its largest surface facing the container support or its contact surface, rests substantially completely on the upper surface of the container support. The upper surface of the container support may be designated as a receiving surface. The container support can be, for example, plate-shaped or dish-shaped and can be substantially rectangular in plan view. The dish-shaped container supports serve substantially to receive the fluid coming out of the container in the event of leakage. However, dish-shaped container supports are possible which have one or more open corners or openings through which the discharge conduits can be directed in the set-up position in order thus to simplify removal from the container. The size of the container support is not limited and can be chosen according to the container size. The shape and size of the container support in plan view corresponds substantially to the shape and size of the container in plan view.

The moving device is designed to move the container support in order to carry out the mixing movement. For this purpose, the moving device is connected to the container support, preferably by means of a movable coupling element. When the container is moved for mixing of the contents of the container, the container support is in a mixing position, and the container positioned thereon is in a mixing position. In the mixing position, the container support, or the receiving surface thereof, is oriented substantially horizontally. More precisely, for mixing, in the mixing position the container support carries out a movement around or in the horizontal plane. Depending upon the type of movement, the mixing device can be designated as a rocker, platform shaker, tumble mixer, circular shaker, vibratory shaker, horizontal shaker, orbital shaker, etc. In the case of a rocker the container support carries out a tilting or rocking movement about a substantially horizontal axis, wherein the container support is initially inclined in a range from approximately 0-15°, preferably in a range from approximately 0-10°, with respect to the horizontal plane, and subsequently in the reverse direction in a range of approximately 0-15°, preferably in a range from approximately 0-10°, with respect to the horizontal plane. This movement of the container support is transmitted to the container, so that an undulating movement of the contents of the container can be generated. However, the mixing movement of the container support does not necessarily have to include an inclination with respect to the horizontal plane, and instead the container support can also be moved back and forth in a linear or circular movement in the horizontal plane and/or while oriented horizontally it can be moved or shaken back and forth in the vertical direction. Combined forms of the types of movement are likewise possible. Thus the mixing position can be changed by the movement of the container support, but lies substantially in the horizontal plane or only deviates slightly therefrom. The container support preferably has a predetermined or predeterminable rest orientation, which is adopted when the container support does not carry out any mixing movement in the mixing position. In the rest orientation the container arranged on the container support is in a rest position. In the rest orientation or rest position the container support or the container is preferably oriented approximately horizontally. The same applies to the mixing position of the container arranged on the container support.

For positioning or fixing of the container on the container support the container support has a positioning device which can be provided in each case on one or more sides of the container support. The positioning device can, for example, have clamps, clamping rails and/or fastening hooks. In particular, the positioning device can enable releasable positioning or fixing of the container on the container support. The positioning device is designed to position the container in a predetermined or predeterminable position at or on the container support, so that the removal side of the container is arranged substantially along a predetermined imaginary line on the container support. The predetermined line is an imaginary line and does not have to be visible on the container support. The removal side of the container, in particular the substantially straight lateral edge of the container interior, extends along this imaginary line on the container support when the container is positioned on the container support by means of the positioning device.

The predetermined line can correspond to a lateral edge of the container support on the removal side, or can extend parallel thereto. In this case the removal pivot axis can also be defined with regard to the lateral edge of the container support, i.e., the removal pivot axis is arranged at an angle of more than 0° to 45°, preferably approximately 1° to approximately 15°, particularly preferably approximately 3° to approximately 10°, with respect to the lateral edge of the container support.

The predetermined line can also correspond to the direction of extension of a clamping rail of the positioning device or can extend parallel thereto. In this case the removal pivot axis can also be defined with regard to the direction of extension of the clamping rail, i.e., the removal pivot axis is arranged at an angle of more than 0° to 45°, preferably approximately 1° to approximately 15°, particularly preferably approximately 3° to approximately 10°, with respect to the direction of extension of the clamping rail.

The container support can have a stop for the removal side of the container, wherein in this situation the predetermined line can correspond to the direction of extension of the stop or can extend parallel thereto. In this case the removal pivot axis can also be defined with regard to the direction of extension of the stop, i.e., the removal pivot axis is arranged at an angle of more than 0° to 45°, preferably approximately 1° to approximately 15°, particularly preferably approximately 3° to approximately 10°, with respect to the direction of extension of the stop.

If the container support has a symmetrical configuration in plan view, the predetermined line can extend in parallel to an axis of symmetry of the container support. In this case the removal pivot axis can also be defined with regard to the axis of symmetry of the container support, i.e., the removal pivot axis is arranged at an angle of more than 0° to 45°, preferably approximately 1° to approximately 15°, particularly preferably approximately 3° to approximately 10°, with respect to the axis of symmetry of the container support.

The container support is mounted pivotably on the moving device and can be pivoted relative to the moving device. This pivoting movement is independent of the mixing movement of the container support and in principle is not carried out during the mixing movement. The pivotability of the container support relative to the moving device enables a displacement of the container support from the mixing position into a removal position. Accordingly, the pivotability of the container support relative to the moving device enables a displacement of the container arranged on the container support from the mixing position into a removal position. The displacement from the mixing orientation or mixing position into the removal orientation or removal position can also be designated as "setting up".

In the removal position the container is set up in such a way that the removal side in the vertical direction is located on the lower side of the container and is inclined toward a removal region of the container. The removal region can be arranged in the region of one of the lower corners of the container, wherein the removal region can be arranged directly in the corner itself or can be arranged on the upper surface or contact surface of the container close to the corner. In the removal position the contact surface of the container is inclined at a steep angle with respect to the horizontal plane, and the removal side of the container forms a lower side or edge of the container. The removal side of the container is inclined with respect to the horizontal plane, but at a flatter angle. When the contact surface is set up approximately perpendicular to the horizontal plane, the angle of inclination of the removal side with respect to the horizontal plane corresponds approximately to the pivot axis angle between the removal pivot axis and the predetermined line on the container support. When the contact surface is inclined at less than 90° with respect to the horizontal plane, the angle of inclination of the removal side with respect to the horizontal plane is less than the pivot axis angle between the removal pivot axis and the predetermined line on the container support. In the removal position the contact surface of the container can be inclined at an angle of 30° to 90°, preferably 35° to 55°, with respect to the horizontal plane.

In other words, in the removal orientation the receiving surface of the container support is inclined at a steep angle with respect to the horizontal plane, and the predetermined line on the container support is likewise inclined with respect to the horizontal plane, but at a flatter angle. When the receiving surface is set up approximately perpendicular to the horizontal plane, the angle of inclination of the predetermined line with respect to the horizontal plane corresponds approximately to the pivot axis angle between the removal pivot axis and the predetermined line. When the receiving surface is inclined at less than 90° with respect to the horizontal plane, the angle of inclination of the predetermined line with respect to the horizontal plane is less than the pivot axis angle between the removal pivot axis and the predetermined line. In the removal orientation the receiving surface of the container support can be inclined at an angle of 30° to 90°, preferably 35° to 55°, with respect to the horizontal plane.

Since in the mixing orientation or rest orientation, i.e., when the container is in the mixing position or rest position, the container support (or the receiving surface thereof) is substantially oriented with respect to the horizontal plane, the above statements apply to the inclinations in relation to the horizontal plane, primarily also to the inclinations in relation to the mixing orientation or rest orientation.

The removal pivot axis is arranged at a pivot axis angle of more than 0° to 45° with respect to the predetermined line of the container support, wherein the smallest angle (i.e., an angle between 0° and 90°) between the removal pivot axis and the predetermined line is meant here. If the removal pivot axis and the predetermined line do not intersect in space, that is to say are skewed, the pivot axis angle should be defined as the angle between the direction vectors of the removal pivot axis and the predetermined line. In other words, the pivot axis angle of the greatest determinable angle is between 0° and 90° between the projected lines of the removal pivot axis and of the predetermined line on all possible planes in space.

The pivot axis angle preferably corresponds to the angle between the lines of the removal pivot axis and the predetermined line projected on the horizontal plane when the container support (or the receiving surface thereof) is oriented with respect to the horizontal plane or when the container support is in the mixing orientation or rest orientation. In other words, the removal pivot axis is inclined within the horizontal plane relative to the predetermined line about the pivot axis angle, and has no inclination relative to the horizontal plane. The container support and/or the moving device can have a pivot bearing which connects the container support to the moving device, wherein the pivot axis of the pivot bearing corresponds to the removal pivot axis.

The oblique arrangement of the removal pivot axis with respect to the predetermined line of the container support advantageously enables the container support and the container positioned thereon to be displaced by means of one single pivoting movement into an advantageous removal orientation or removal position. In the removal orientation the container support is set up relative to the horizontal plane. The container is preferably attached and removed in the horizontal position. However, it cannot be ruled out that the container is also positioned or fixed in the removal position on the container support. However, this is easier in the rest orientation. Furthermore, in the removal position the removal side of the container is inclined with respect to a removal region, so that the removal region is always arranged at the lowest point of the container. As a result, cells or metabolites, which can settle in the fluid or the suspension due to gravity, advantageously collect in the removal region, which additionally simplifies the removal.

The removal pivot axis is preferably arranged at a pivot axis angle of approximately 1° to approximately 15°, particularly preferably approximately 3° to approximately 10°, with respect to the predetermined line.

At a pivot axis angle which is too small, in the removal position the inclination of the removal side toward the removal region is too small for good sedimentation. On the other hand, at a pivot axis angle which is too large, the positioning or fixing of the container on the container support can be difficult, since the container, which can have a substantial weight, must be positioned on the container support at an angle which deviates considerably from the horizontal plane. It has been shown that a pivot axis angle of approximately 1° to approximately 15°, particularly preferably approximately 3° to approximately 10°, is particularly advantageous for the collection of products in the removal region and for simple positioning of the container on the container support.

The moving device is preferably designed to move the container support back and forth about a substantially horizontal rocking axis, wherein the rocking axis is arranged substantially parallel to the predetermined line.

In the rocking movement the container support is initially inclined by approximately 2° to 15° with respect to the horizontal plane, and is subsequently inclined in the reverse direction by approximately 2° to 15° with respect to the horizontal plane. This movement of the container support can be carried out repeatedly and can be transmitted to the container, so that a continuous undulating movement of the contents of the container can be generated. The rocking axis can be predetermined by the moving device. The rocking axis is preferably arranged centrally relative to the container support or to the container positioned thereon, so that the path traveled in the vertical direction by the removal side in the tilting movement corresponds approximately to the path traveled in the vertical direction by the side of the container opposite the removal side. The rocking axis can be spaced apart from the receiving surface of the container support in the vertical direction. The rocking axis is arranged substantially parallel to the predetermined line, so that the removal pivot axis can also be defined with regard to the rocking axis, i.e., the removal pivot axis is arranged at an angle of more than 0° to 45°, preferably approximately 1° to approximately 15°, particularly preferably approximately 3° to approximately 10°, with respect to the rocking axis.

The moving device preferably has a movable coupling element, which for movement of the container support is connected to the container support, wherein the container support is mounted pivotably about the removal pivot axis on the coupling element, so that the container support can be displaced by means of a pivoting movement from a mixing orientation into a removal orientation.

The coupling element can be driven or moved by a drive means of the moving device. The coupling element can project upward from a base of the moving device. The container support is connected by means of the coupling element to the moving device, so that the movement of the coupling element can be transmitted to the container support and further onto the container.

The positioning device preferably has at least one clamping rail which extends substantially along the predetermined line or parallel thereto.

In particular in the case of a foil bag, one side of the container can advantageously be fixed on the container support by means of the clamping rail. Preferably a clamping rail is provided on the removal side of the container and a clamping rail is provided on the side of the container opposite the removal side. At the corresponding points the container can have clips or rails which co-operate with the clamping rails. In a particularly preferred embodiment the container has, on its periphery on at least two sides, stable bars or rods which are inserted in clips and correspond to the clamping rails of the container support and are gripped thereby. Thus the container is retained with the aid of the bars fixed in the clamping rails. The stable bars or rods are preferably made of plastic.

The positioning device preferably has at least one fastening hook which is arranged substantially along the predetermined line or parallel thereto.

The fastening hook enables particularly simple fixing of a side of the container to the container support. The fastening hook can have a shape extending in the width direction and/or a plurality of fastening hooks can be arranged along the predetermined line or parallel thereto. Preferably a fastening hook is provided on the removal side of the container and a fastening hook is provided on the side of the container opposite the removal side. The container can have recesses, in particular holes and/or slots, into which the fastening hook(s) can be introduced.

The container support is preferably dish-shaped, and an inner edge of the dish-shaped container support extends substantially along the predetermined line or parallel thereto.

The dish shape of the container support enables particularly good support in the case of containers in the form of foil bags, since in the filled and inflated state these bags can have a contact surface which corresponds to the dish shape. Furthermore, the dish shape enables a good lateral retention of the container, which is important during the mixing movement and during set-up. In the event of leakages, a closed dish offers additional security against the further spread of contaminants with the fluid coming out of the container. Since in this case the container bears against the dish-shaped receiving surface of the container support, the inner edge of the container support extends along the predetermined line or parallel thereto. In a further embodiment, the dish-shaped container support is open at one or more corners, so that feed and/or discharge conduits as well as connections for various sensor elements can be conveniently routed in these regions.

The coupling element preferably has a contact region which bears against an underside of the container support and supports it when the container which is positionable on the container support is located in the mixing position.

In other words, the contact region of the coupling element constitutes a stop for the container support when the container support is displaced from the removal orientation into the mixing orientation. In the mixing orientation the container support is oriented substantially horizontally by the contact region. In this case the container support is supported, on the one hand, by the pivot bearing between the container support and the coupling element and by the contact region of the coupling element.

The coupling element is preferably substantially plate-shaped, wherein the removal pivot axis is arranged at one end of the plate-shaped coupling element.

"Substantially plate-shaped" means that the coupling element has a planar configuration. However, the coupling element can have recesses or can be a frame structure. The plate-shaped coupling element is preferably oriented substantially with respect to the horizontal plane, and the removal pivot axis or the pivot bearing is arranged at one end of the coupling element. In the mixing orientation the container support can bear with its underside against the coupling element, in particular the contact region thereof, wherein the container support is oriented parallel to the coupling element.

The mixing device preferably comprises a set-up mechanism, which makes it possible to fix the container support at a predetermined or predeterminable set-up angle relative to the moving device.

The set-up mechanism is preferably connected to the coupling element and makes it possible to set up and/or fix the container support at a predetermined or predeterminable set-up angle relative to the coupling element. The set-up mechanism can be driven hydraulically, pneumatically and/or electrically and can enable set-up and/or fixing of the container support at a predetermined or predeterminable set-up angle. The set-up mechanism is preferably arranged between the coupling element and the container support.

The set-up mechanism preferably has a lever for locking or a locking lever which is arranged pivotably on the moving device and which supports the container support when the container which is positionable on the container support is located in the removal position.

The locking lever is preferably arranged pivotably on the coupling element. The locking lever enables a particularly simple set-up mechanism, since the container support, in particular the underside thereof, does not have to be specifically configured. In the mixing orientation the locking lever is oriented substantially horizontally and substantially in the same plane as the container support and/or the coupling element. By pivoting of the locking lever the container support is raised and set up pivotably about the removal pivot axis, wherein the locking lever slides along on the underside of the container support. The pivot axis of the locking levers is preferably arranged approximately parallel to the removal pivot axis.

An exemplary embodiment of the present invention is described in greater detail with reference to the appended drawings.

DETAILED DESCRIPTION

Figure 1:
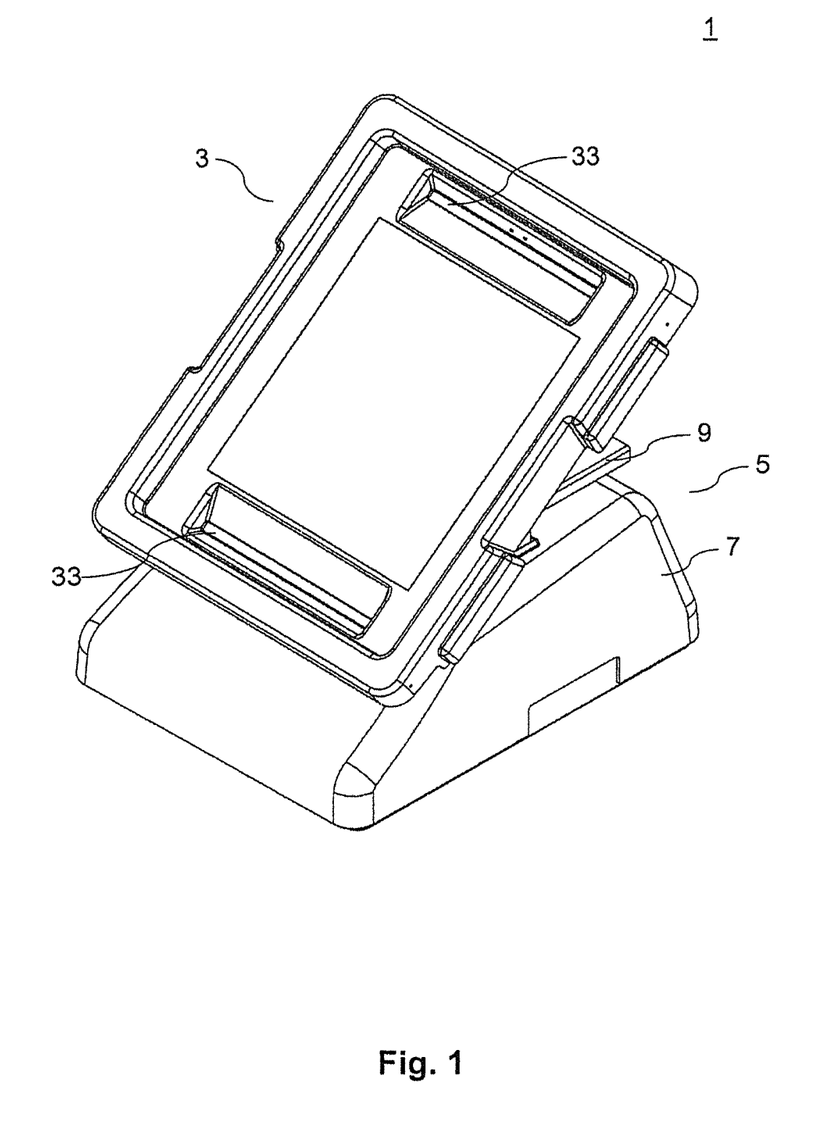
FIG. 1 shows a perspective view of a mixing device according to an exemplary embodiment.

FIG. 1 shows a perspective view of a mixing device 1 according to an exemplary embodiment. The mixing device 1 comprises a container support 3 which is arranged on a moving device 5. The moving device 5 comprises a base 7 and a coupling element 9. The container support 3 is connected to the coupling element 9 and is mounted so as to be pivotable thereon about a removal pivot axis. The removal pivot axis is not shown in FIG. 1. In the state shown in FIG. 1, the container support 3 is inclined with respect to the horizontal plane and therefore is not in the mixing position but in the removal position or an intermediate position between the mixing position and the removal position. The container support 3 has a plate or dish shape and has a depression or recess 33 in each case in its lower and upper region. The recess 33 serves to accommodate sensors, but can also have holes for conduits and/or cables to pass through.

Figure 2:
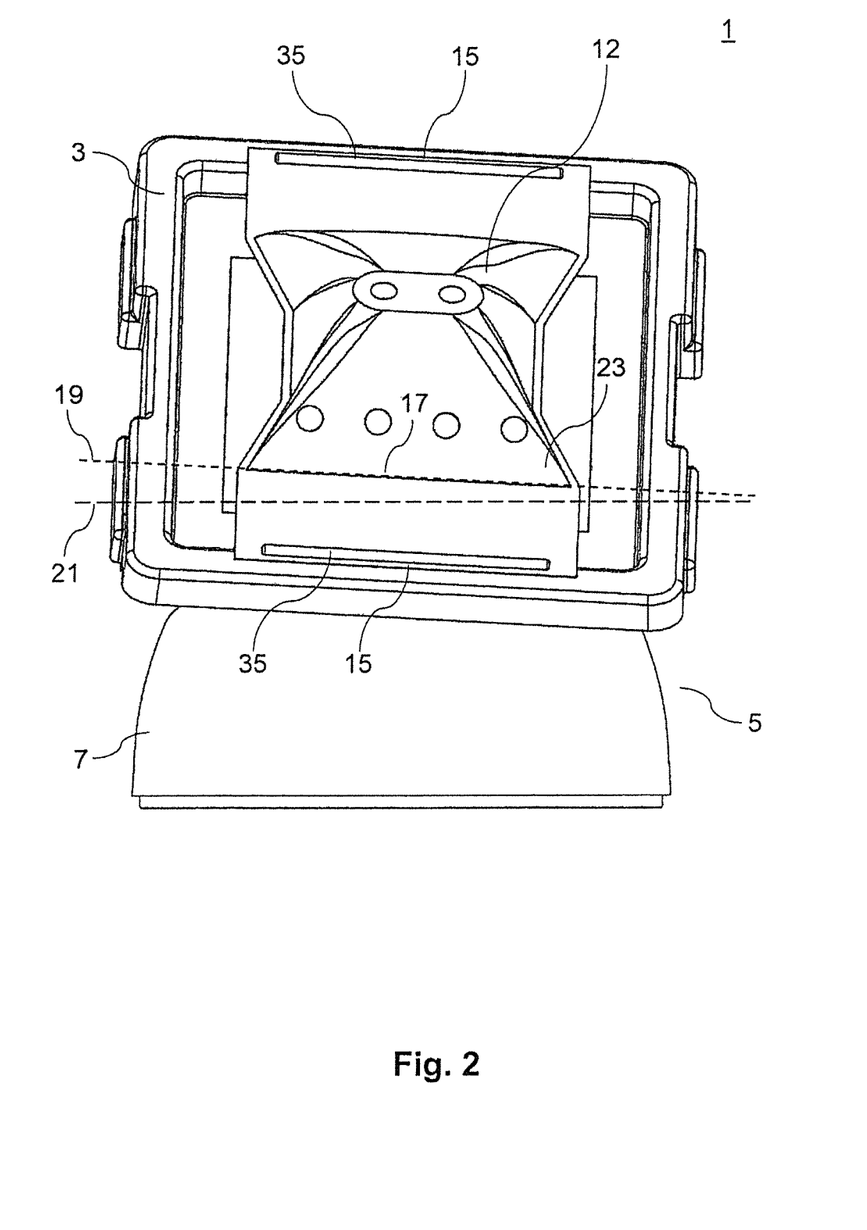
FIG. 2 shows a front view of the mixing device with a container positioned thereon.
Figure 3:
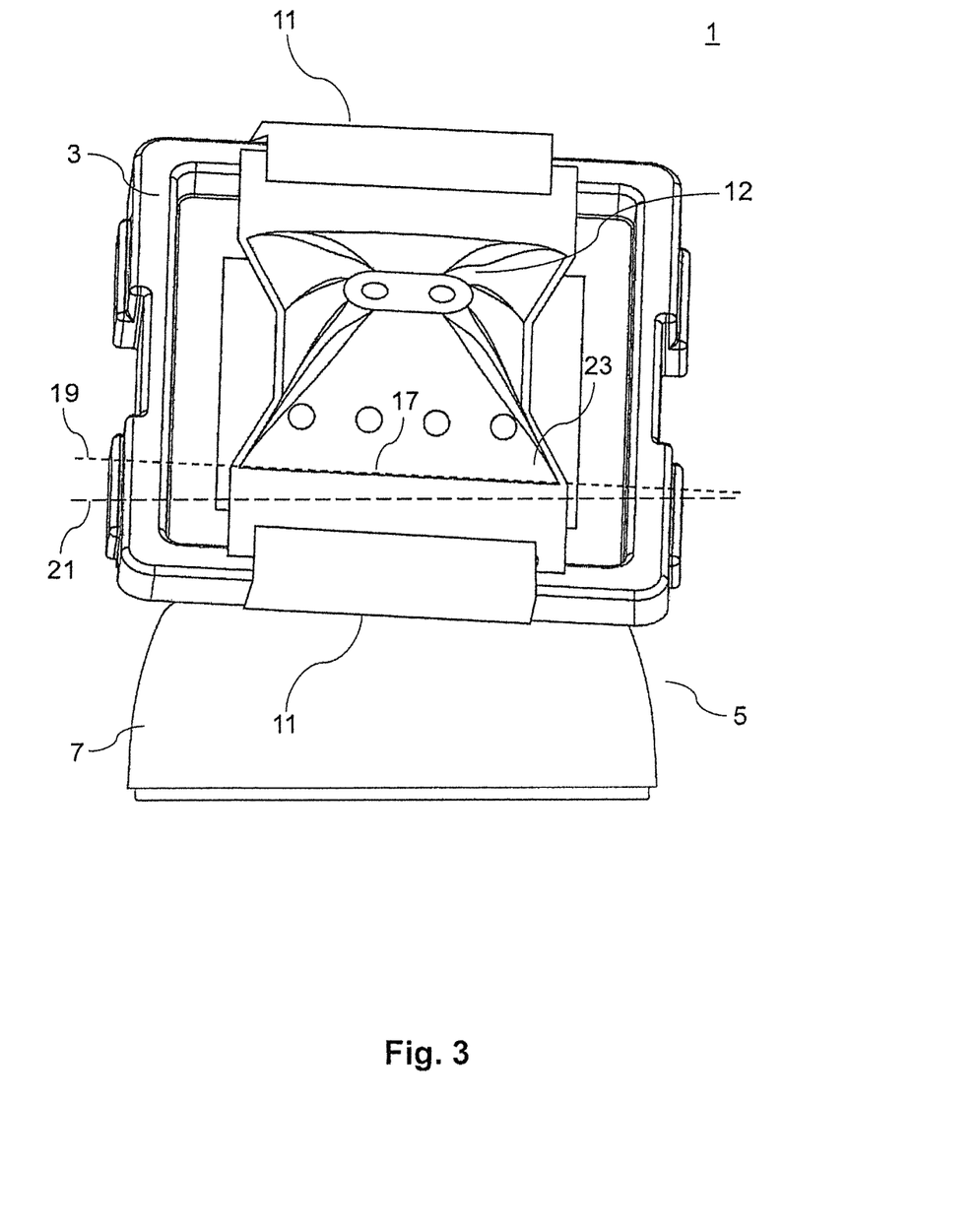
FIG. 3 shows a front view of the mixing device with a container positioned thereon and with clamping strips.

FIG. 2 and FIG. 3 each show the mixing device 1 in a front view, wherein a container 12 in the form of a foil bag or bioreactor bag is arranged on the container support 3. The positioning device 11 is shown in FIG. 3, in FIG. 2 it is hidden. The container 12 is positioned or fastened on the container support 3 with two opposing ends 15 by means of the positioning device 11. In the illustrated embodiment the container 12 is fastened by means of flexible rods or clamping rods 35 (also referred to as "rods") which are inlaid in clips at the ends of the container 12, and fastened to the positioning device 11 in the form of clamping strips. The clamping rods 35 can be welded on or in the container 12 or inserted loosely in plastic clips. Due to the positioning device 11, in particular in interaction with the clamping rods 35, the position of the container 12 on the container support 3 is predetermined, and the removal side 17 of the container 12 is arranged along the predetermined line 19 of the container support 3. The removal pivot axis 21 is inclined relative to the predetermined line 19 or the removal side 17. However, the precise pivot axis angle is not discernible from the predetermined viewing angle in FIG. 2 and FIG. 3. This would only be discernible if the container support 3 were set up perpendicular to the horizontal plane, that is to say arranged perpendicular to the viewing direction in FIG. 2 and FIG. 3. In the exemplary embodiment the removal pivot axis 21 is oriented horizontally. The removal pivot axis 21 is predetermined by the pivot bearing between the container support 3 and the coupling element 9. If no mixing movement is carried out the removal pivot axis 21 is stationary, in particular the removal pivot axis 21 does not move when the container support 3 is moved from the mixing position into the removal position. In the state shown in FIG. 2 and FIG. 3 the container support 3 is in the removal position or the intermediate position, i.e., the container 12 is in the removal position or in an intermediate position. In this case is the removal side 17 is inclined with respect to the horizontal plane, in particular with respect to the removal region 23.

Figure 4:
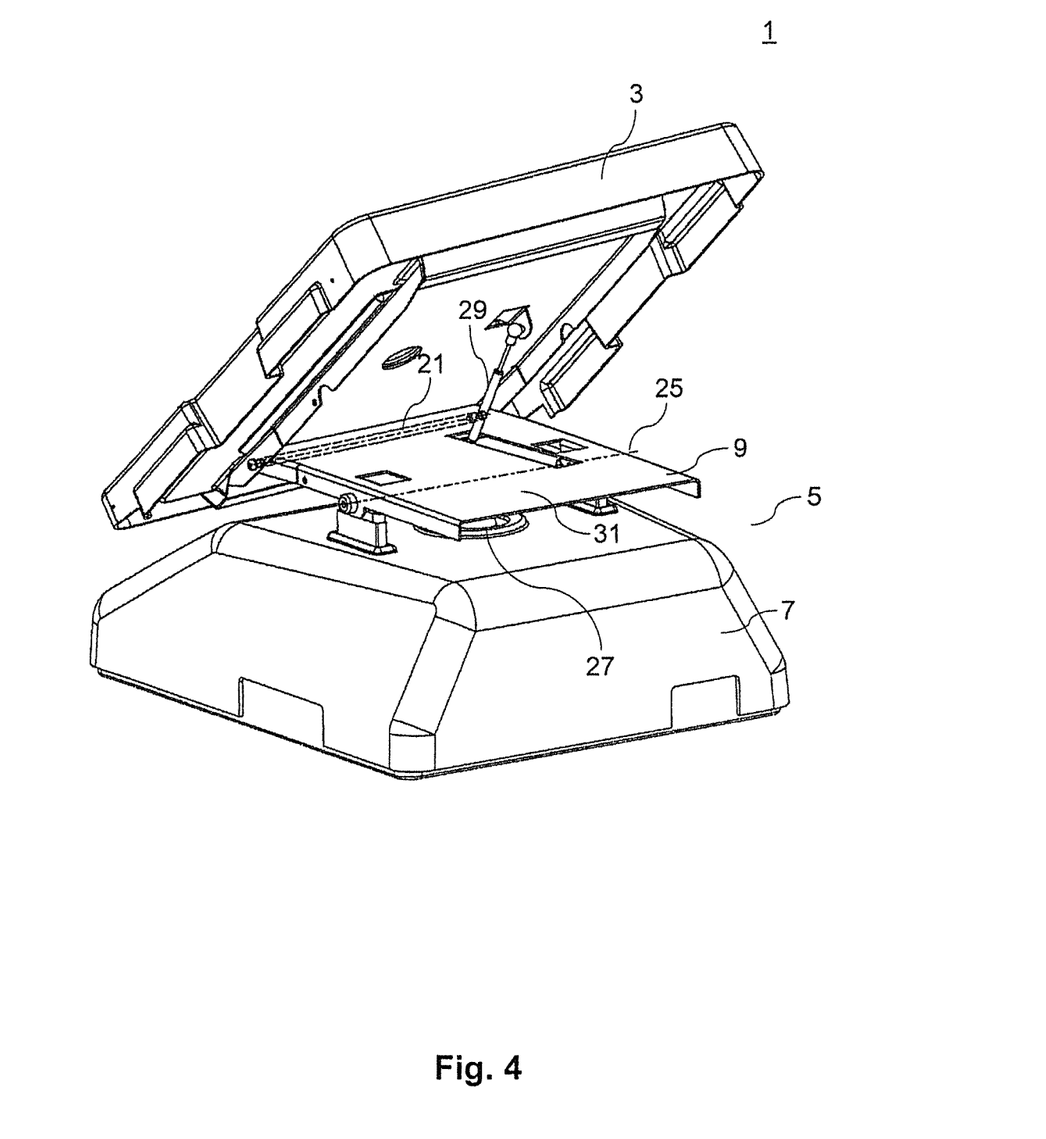
FIG. 4 shows a further perspective view of the mixing device.

FIG. 4 shows a further perspective view of the mixing device 1 from another angle. The coupling element 9 is plate-shaped and is mounted on the base 7 of the moving device 5 so as to be pivotable about the tilting axis 25. The drive 27 generates a tilting movement of the coupling element 9 about the tilting axis 25 for generating the mixing movement. The removal pivot axis 21 is arranged transversely with respect to the tilting axis 25 at an end of the coupling element 9. Thus the removal pivot axis 21 and the tilting axis 25 lie in the same horizontal plane. However, the removal pivot axis 21 is inclined about the pivot axis angle with respect to the tilting axis 25. However, the removal pivot axis 21 is also inclined about the pivot axis angle with respect to the predetermined line. In the mixing position the predetermined line and the tilting axis 25 are disposed parallel to one another. In the mixing position the underside of the container support 3 lies on the bearing surface region 31 of the coupling element 9 and is supported thereby. For setting up and/or fixing the container support 3, the mixing device 1 has a set-up mechanism 29 in the form of a gas pressure spring 29. The gas pressure spring 29 is fastened with one end to the coupling element 9 and with the other end to the underside of the container support 3.

Figure 5:
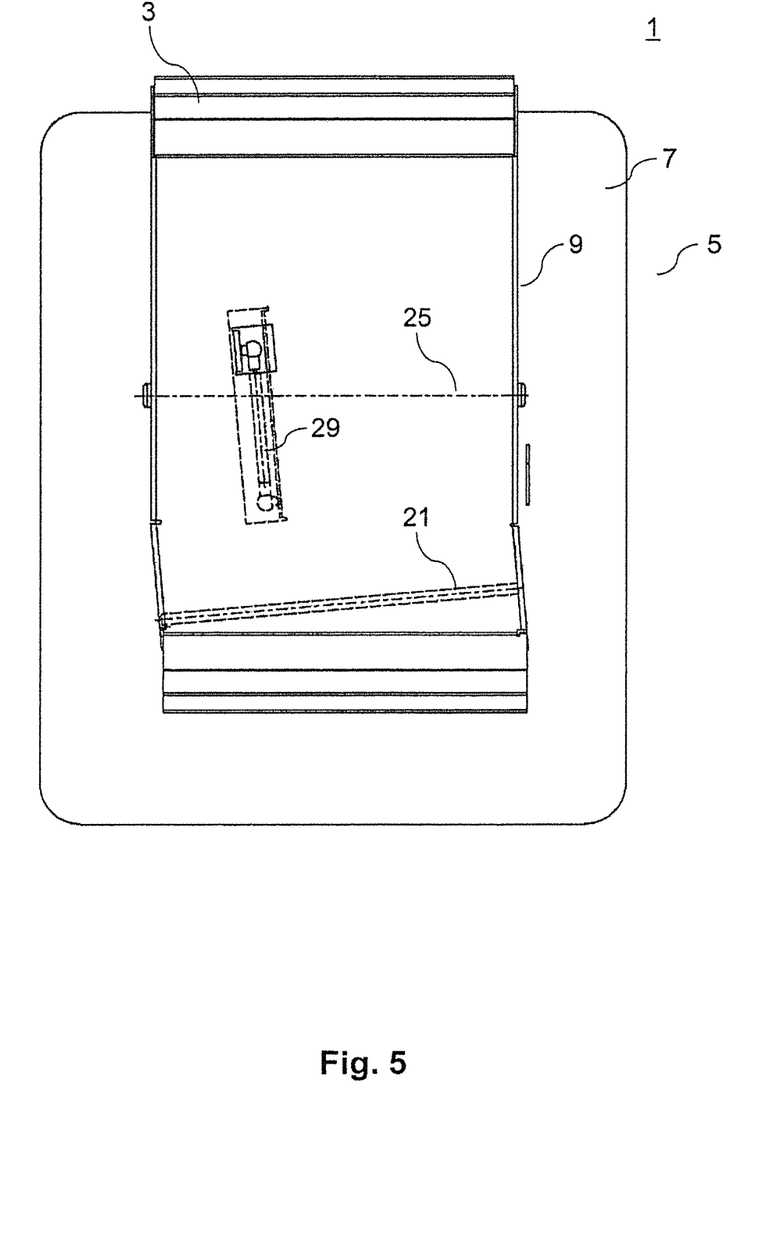
FIG. 5 shows a plan view of the mixing device.

FIG. 5 shows the mixing device 1 in a plan view. The removal pivot axis 21 is arranged inclined by the pivot axis angle with respect to the tilting axis 25. The gas pressure spring 29 is oriented in such a way that the container support 3 can be moved from the mixing position into the removal position by linear movement of the gas pressure spring 29. For this purpose, in the starting position, i.e., when the container support 3 is in the mixing position and the gas pressure spring 29 is arranged parallel to the coupling element 9 in the horizontal plane, the gas pressure spring 29 is inclined approximately about the pivot axis angle with respect to a line which is perpendicular to the tilting axis 25 and/or the predetermined line. In other words, the gas pressure spring pivot axis is arranged approximately parallel to the removal pivot axis 21.

LIST OF REFERENCE NUMERALS 1 mixing device
3 container support
5 moving device
7 base of the moving device
9 coupling element
11 positioning device
12 container
15 container end
17 removal side
19 predetermined line
21 removal pivot axis
23 removal region 25 tilting axis
27 drive
29 set-up mechanism, gas pressure spring
31 contact region
33 recess
35 clamping rod

The invention claimed is:

1. A mixing device (1) for mixing contents of a container (12), the container having a removal side (17) that defines a side of the container (12) designated for collection and removal of the contents of the container (12), comprising:
   a container support (3) configured for supporting the container (12); and
   a moving device (5) connected to the container support (3) and operative for generating movement of the container support (3) so that the contents of the container (12) can be mixed when the container support (3) is in a mixing position; wherein:
   the container support (3) has a positioning device (11) designed to position the container (12) in a predetermined or predeterminable position on the container support (3), so that the removal side (17) of the container (12) is arranged substantially along a predetermined line (19) of the container support (3),
   the container support (3) is mounted to be pivotable about a removal pivot axis (21) relative to the moving device (5) to move the container (12), which can be positioned on the container support (3), into a removal position,
   the removal pivot axis (21) is arranged at a pivot axis angle of over 0° to 45° to the predetermined line (19) of the container support (3) so that the container (12) positioned on the container support (3) can be moved from the mixing position by means of a pivoting movement of the container support (3) about the removal pivot axis (21) into the removal position in which the removal side (17) is located on a lower side of the container (12) and also inclined toward a removal region (23) on the removal side (17) of the container (12).

2. The mixing device (1) of claim 1, wherein the removal pivot axis (21) is arranged at a pivot axis angle of approximately 1° to approximately 15° with respect to the predetermined line (19).

3. The mixing device (1) of claim 1, wherein the moving device (5) is designed to move the container support (3) back and forth about a substantially horizontal rocking axis (25), wherein the rocking axis (25) is arranged substantially parallel to the predetermined line (19).

4. The mixing device (1) of claim 1, wherein the moving device (5) has a movable coupling element (9) connected to the container support (3), the container support (3) being mounted pivotably about the removal pivot axis (21) on the coupling element (9), so that the container support (3) can be pivoted relative to the coupling element (9) from a mixing orientation into a removal orientation.

5. The mixing device (1) of claim 1, wherein the positioning device (11) has at least one clamping rail that extends substantially along the predetermined line (19) or parallel thereto.

6. The mixing device (1) of claim 1, wherein the positioning device (11) has at least one fastening hook that is arranged substantially along the predetermined line (19) or parallel thereto.

7. The mixing device (1) of claim 1, wherein the container support (3) is dish-shaped, and an inner edge of the dish-shaped container support (3) extends substantially along the predetermined line (19) or parallel thereto.

8. The mixing device of claim 4, wherein the coupling element (9) has a contact region (31) that bears against an underside of the container support (3) and supports the container support (3) when the container, which is positionable on the container support (3), is in the mixing position.

9. The mixing device (1) of claim 4, wherein the coupling element (9) is substantially plate-shaped, and the removal pivot axis (21) is arranged at one end of the plate-shaped coupling element (9).

10. The mixing device (1) of claim 1, further comprising a set-up mechanism (29) configured to fix the container support (3) at a predetermined or predeterminable set-up angle relative to the moving device (5).

11. The mixing device (1) of claim 10, wherein the set-up mechanism (29) has a locking lever arranged pivotably on the moving device (5) and that supports the container support (3) when the container (12), which is positionable on the container support (3), is located in the removal position.

* * * * *